(12) United States Patent
Panetta et al.

(10) Patent No.: US 11,076,950 B2
(45) Date of Patent: Aug. 3, 2021

(54) ELECTROLARYNX DEVICES AND USES THEREOF

(71) Applicant: TRUSTEES OF TUFTS COLLEGE, Medford, MA (US)

(72) Inventors: Karen Panetta, Rockport, MA (US); Chiamaka Chima, Onitsha (NG); Paul Lehrman, Medford, MA (US)

(73) Assignee: TRUSTEES OF TUFTS COLLEGE, Medford, MA (US)

( * ) Notice: Subject to any disclaimer, the term of this patent is extended or adjusted under 35 U.S.C. 154(b) by 0 days.

(21) Appl. No.: 16/609,813

(22) PCT Filed: Apr. 30, 2018

(86) PCT No.: PCT/US2018/030182
§ 371 (c)(1),
(2) Date: Oct. 31, 2019

(87) PCT Pub. No.: WO2018/204252
PCT Pub. Date: Nov. 8, 2018

(65) Prior Publication Data
US 2020/0069414 A1  Mar. 5, 2020

Related U.S. Application Data

(60) Provisional application No. 62/492,526, filed on May 1, 2017.

(51) Int. Cl.
*A61F 2/20* (2006.01)
*G10L 25/51* (2013.01)
(Continued)

(52) U.S. Cl.
CPC ............... *A61F 2/20* (2013.01); *G10L 13/00* (2013.01); *G10L 25/51* (2013.01); *H04R 1/14* (2013.01);
(Continued)

(58) Field of Classification Search
USPC ......... 381/58, 70, 71.6, 71.9, 102, 104, 106, 381/110, 120, 151
See application file for complete search history.

(56) References Cited

U.S. PATENT DOCUMENTS 3,878,748 A * 4/1975 Spence .................... G10H 3/24
84/723
5,326,349 A 7/1994 Baraff
(Continued)

FOREIGN PATENT DOCUMENTS

WO  2012/112033 A1  8/2012
WO  2018/204252 A1  11/2018

OTHER PUBLICATIONS

International Search Report of related PCT/US2018/030182, dated Jul. 20, 2018, 9 pages.
(Continued)

*Primary Examiner* — Yosef K Laekemariam
(74) *Attorney, Agent, or Firm* — Casimir Jones, S.C.; Tanya A. Arenson (57) ABSTRACT

The present disclosure relates to electrolarynx devices, systems, and their use. In particular, the present disclosure relates to methods and compositions (e.g., devices) that provide electrolarynx (EL) users with improved speech quality.

8 Claims, 10 Drawing Sheets

(51) Int. Cl.
*H04R 1/14* (2006.01)
*H04R 3/00* (2006.01)
*G10L 13/00* (2006.01)

(52) U.S. Cl.
CPC .......... *H04R 3/00* (2013.01); *A61F 2002/206* (2013.01); *A61F 2250/0002* (2013.01)

(56) References Cited

U.S. PATENT DOCUMENTS

| | | | |
|---|---|---|---|
| 5,812,681 A | | 9/1998 | Griffin |
| 5,888,187 A | * | 3/1999 | Jaeger .................. A61B 5/0031 600/23 |
| 2008/0167868 A1 | * | 7/2008 | Kanevsky ............... G10L 15/24 704/233 |
| 2011/0190881 A1 | | 8/2011 | Russell et al. |
| 2013/0294613 A1 | | 11/2013 | Nagel et al. |
| 2014/0358551 A1 | | 12/2014 | Liu et al. |
| 2017/0212723 A1 | * | 7/2017 | Atarot ..................... G10L 15/28 |

OTHER PUBLICATIONS

Uemi N, Ifukube T, Takahashi M, Matsushima J. Design of a new electrolarynx having a pitch control function. IEEE Workshop on Robot and Human.1994. pp. 198-202.

* cited by examiner

For Part 1:

9a) 
Breath Circuit for Stoma
EL

9b) 
Neck
EL
Stoma
Breath circuit for Stoma

9c) 
EL
Detachable Breath circuit for Stoma

For Part 2:

9d) 
Neck
Neck & Jaw – worn Data Acquisition Circuitry
Wireless or Wired
Smart speech circuit
+
Pocket Speaker

FIG. 10

ELECTROLARYNX DEVICES AND USES THEREOF

CROSS-REFERENCE TO RELATED APPLICATION

The present application is a 371 U.S. National Phase Entry of pending International Application No. PCT/US2018/030182, filed Apr. 30, 2018, which claims priority to U.S. Provisional Patent Application Ser. No. 62/492,526, filed May 1, 2017, which are hereby incorporated by reference in their entireties.

FIELD OF THE DISCLOSURE

The present disclosure relates to electrolarynx devices, systems, and their use. In particular, the present disclosure relates to methods and compositions (e.g., devices) that provide electrolarynx (EL) users with improved speech quality.

BACKGROUND

Normal human speech is in part facilitated by the larynx, an organ just below the vocal tract that helps to control the pitch and volume of the voice. When a patient's larynx must be surgically removed—often due to laryngeal cancer—the laryngectomee loses the ability to speak in the usual manner. Electrolarynx (EL) devices are often used by such patients to communicate; these medical instruments act as artificial larynxes by producing the mechanical vibration necessary to excite the remaining vocal tract. The sound waves that are produced by this vibration are then articulated by the teeth, tongue, and lips.

Audible speech is produced by this method, but EL speech is far less intelligible than normal human speech. Rather than using the larynx as the sound source, EL speech uses a crude, buzzing diaphragm, which does not produce a waveform with the same acoustic characteristics that are present in a human voice. This diaphragm, which is held against the neck so that the mechanical vibration is transmitted to the vocal tract, produces a sound that is neither pleasant nor particularly clear.

There is a great need to improve current EL designs so that laryngectomees can communicate with a level of expression and intelligibility that is enjoyed by the normal population.

SUMMARY

The present disclosure relates to electrolarynx devices, systems, and their use. In particular, the present disclosure relates to methods and compositions (e.g., devices) that provide electrolarynx (EL) users with improved speech quality.

In some embodiments, the present disclosure provides an electrolaynx device or system, comprising: a) a sensor configured to be placed in the stoma or on the neck of a human subject; b) a control element configured to obtain signal from the sensor and translate the signal into speech; and c) a speaker configured to amplify the speech. In some embodiments, the control element is configured to turn the speaker on when the subject is talking and turn the speaker off when the subject is silent. In some embodiments, the control element comprises one or more of an electrical circuit, a computer processor, or computer memory. In some embodiments, the control element is further configured to perform articulatory pattern recognition of the subject's speech. In some embodiments, the device is controlled by a sensor that senses the subject's breath. In some embodiments, the device utilizes a sensor that senses movement of the jaw. In some embodiments, the signal is transmitted from the sensor to the control element via an electrical cable.

Further embodiments provide a method of generating artificial speech, comprising: contacting the device with a subject's stoma under conditions such that said device generates speech and transmits the speech through the speaker of the device. In some embodiments, the subject lacks a larynx. In some embodiments, the subject has previously been diagnosed with oral cancer. In some embodiments, the method is performed hands free.

Additional embodiments are described herein.

DETAILED DESCRIPTION

The present disclosure relates to electrolarynx devices, systems, and their use. In particular, the present disclosure relates to methods and compositions (e.g., devices) that provide electrolarynx (EL) users with improved speech quality.

With the surgical removal of the natural larynx, there is a loss of the vocal cord and the connection thereof with the trachea. Laryngectomees therefore lack phonation due to this missing air-pressure-modulating functionality and hence have to undergo speech or voice rehabilitation.

There are three methods of voice rehabilitation after laryngectomy: esophageal speech, tracheo-esophageal speech, and electrolaryngeal speech. Considering its ease of use compared to the other alternatives, the electronic larynx device (electrolarynx) is the most widely adopted for voice rehabilitation after laryngectomy. Its limitations include distortion and mechanical perception demonstrated by the robotic nature of the speech produced with the device (this leads to difficulty in comprehension for the listener and unwanted attention to the user), confusion with voiced and voiceless pairs especially at the start of sentences hence reduced speech intelligibility, inability to track and match speech prosody as the electrolaryngeal speech sounds monotonous without the needed inflections (this is especially evident when asking questions or in heavily tonal languages e.g. the Igbo language and many East Asian languages), limited speech intensity (the amplitude is relatively lower than laryngeal speech and can be easily drowned in noisy environment), and inconvenience from the hand-held nature (EL users cannot simultaneously talk while using both of their hands).

The anatomy changes after a laryngectomy. After a total laryngectomy, the individual is breathing through the stoma where the tracheostomy opens in the neck. There is no longer a connection between the trachea and the mouth and nose. These individuals are termed total neck breathers. After a partial laryngectomy, the individual breathes mainly through the stoma, but a connection still exists between the trachea and upper airways; these individuals are able to breathe air through the mouth and nose. They are therefore termed partial neck breathers. The extent of breathing through the upper airways in these individuals varies and a tracheostomy tube is present in many of them. Ventilation and resuscitation of total and partial neck breathers is through their stoma; however, in these individuals the mouth should be kept closed and the nose sealed to prevent air escape.

People do not keep track of their pitch, volume, and on/off or pauses in-between words when speaking. Existing devices use a capacitive slider or pressure knob that require an extreme level of manual dexterity and consciousness which is not quite reasonable in addition to other disadvantages (e.g. charge buildup). In addition, existing devices do not mimic pitch. Pitch is a parameter that is very difficult to estimated externally hence it is important to use the human's signal as control signals for the pitch adjustments.

One of the distinguishing features of devices described herein is that they are not a corrective measure as many other techniques that aim to reverse-engineer the electrolarynx in order to make it sound better. The devices described herein instead generate accurate information from the sensor in the stoma to accurately form the speech. This can also eliminate the use of square waves for modulation, which is by itself a source of distortion to the speech produced.

Accordingly, provided herein is an electrolarynx that overcomes many of the limitations of existing devices. In some embodiments, the non-ideal excitation sound of the electrolarynx is corrected. In some embodiments, devices described herein utilize a subsystem to fix the voice/voiceless indistinguishability by creating a synchronous on/off circuitry using human breath to turn on the electrolarynx at the onset of speech and turn it off when speech is over. By so doing, the buzz which would have otherwise filled in the spectral valley of the region of silence is eliminated that makes a "voiceless sound" be perceived as "voiced' in existing devices. In addition, in some embodiments, the sensed-human breath "amplitude information" is used to control the speech volume.

In some embodiments, the frequency part of the sensed human breath is used to control speech pitch (See e.g., UEMI et al. (1994)).

In some embodiments, devices described herein encode speech articulatory patterns into bits recognizable as inputs to ASR systems for clearer communication. (e.g., flex-sensors with resistors are used to measure jaw excursions (e.g., by use of an accelerometer placed underneath the jaw) and then the info is encoded into bits and fed into a microcontroller which is used to "switch" the speech into "normal sounding speech").

Figure 8:
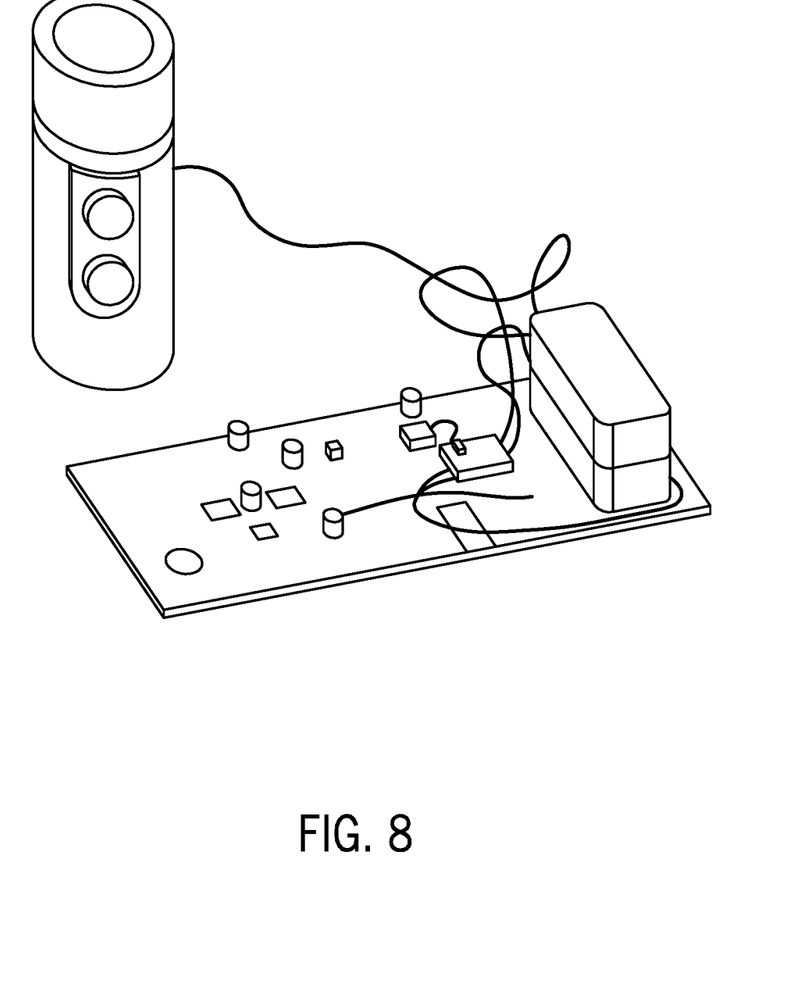
FIG. 8 shows a photograph of an exemplary device of embodiments of the present disclosure.
Figure 9:
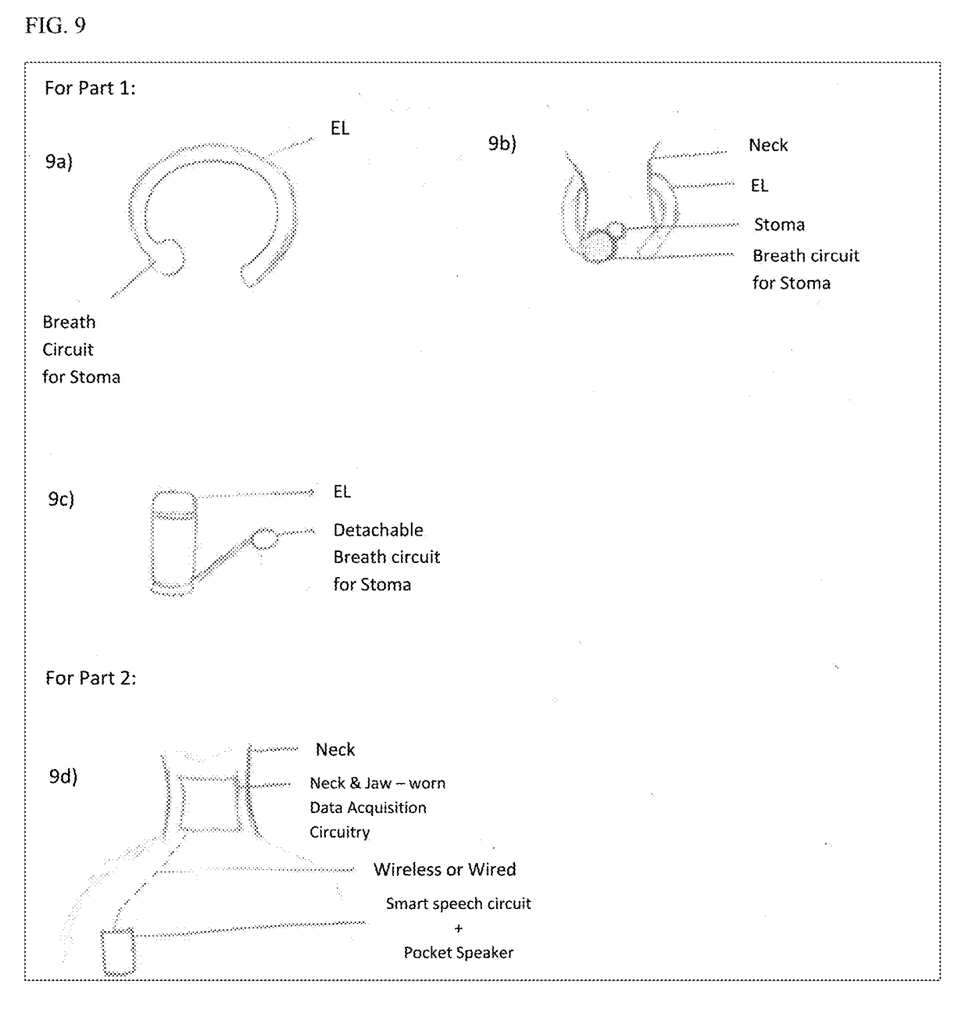
FIG. 9 shows a photograph of an exemplary device of embodiments of the present disclosure.
Figure 10:
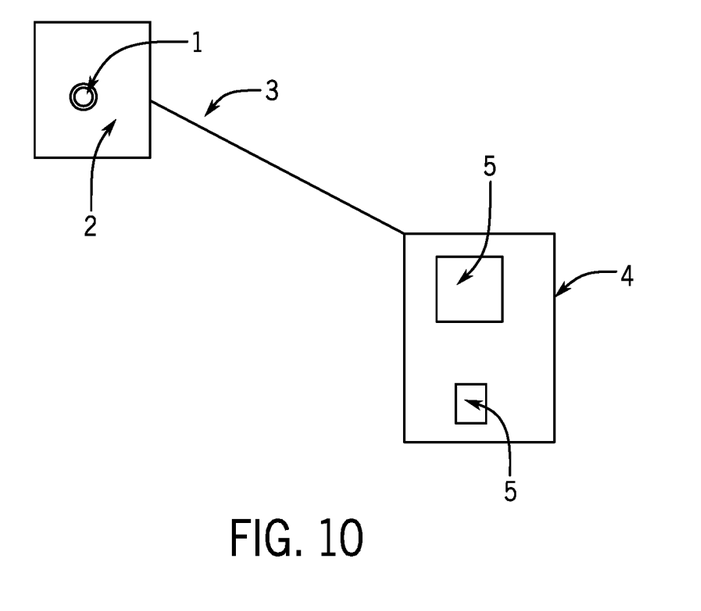
FIG. 10 shows a schematic of an exemplary device of embodiments of the present disclosure.

An exemplary device is described in FIGS. 8-10. The figures shows a throat of a subject 2 with a stoma sensor 1 embedded therein or worn as a neck brace. Information from the sensor is transmitted via wire 3 or wirelessly to the remote smart speech (e.g., electrolaynx) component 4. The smart speech circuit 4 comprises a control element 5 and speaker 6. The control element 5 comprises, for example, electrical circuits, a computer processor and computer memory (See e.g., FIGS. 3-6 for exemplary electrical circuits) that translate signals from the stoma sensor into sound. The control element 5 further senses when speech starts and stops and silences the speaker 6 accordingly.

Figure 7:
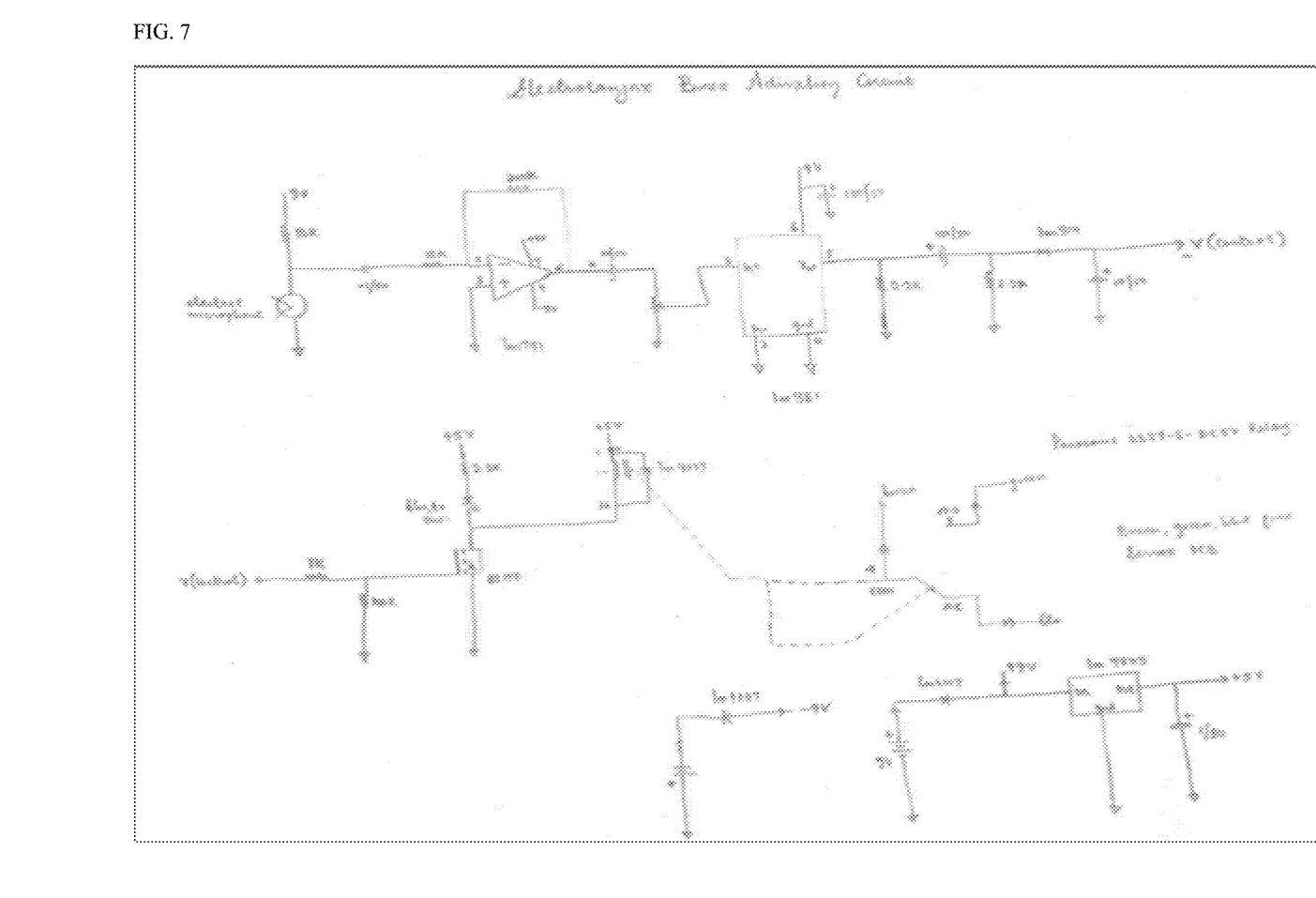
FIG. 7 shows electrical circuits of electrolarynx buzz activation circuit (stoma sensor circuit) of exemplary devices of embodiments of the present disclosure.

The control element 5 senses via information from the stroma sensor 1 when speech starts and stops and silences the speaker 6 accordingly. FIG. 8 shows an exemplary sensor 1. FIG. 7 shows the circuitry for information from the stoma sensor. FIG. 9 shows a diagram of the stroma sensor and related components. FIG. 9 a-c shows an electrolarynx buzz activation circuit (stoma sensor circuit) and stoma sensor. In some embodiments, systems utilize a mini-mic or mini-pressure sensor. In some embodiments, the entire electolarynx, including motion sensor, is strapped to the neck. Such a system is completely hands-free in operation.

FIGS. 3-6 shows circuitry for a sensor that senses jaw movements/excursions rather than breath and translates it to speech. FIG. 9D shows a diagram of such a system.

Figure 1:
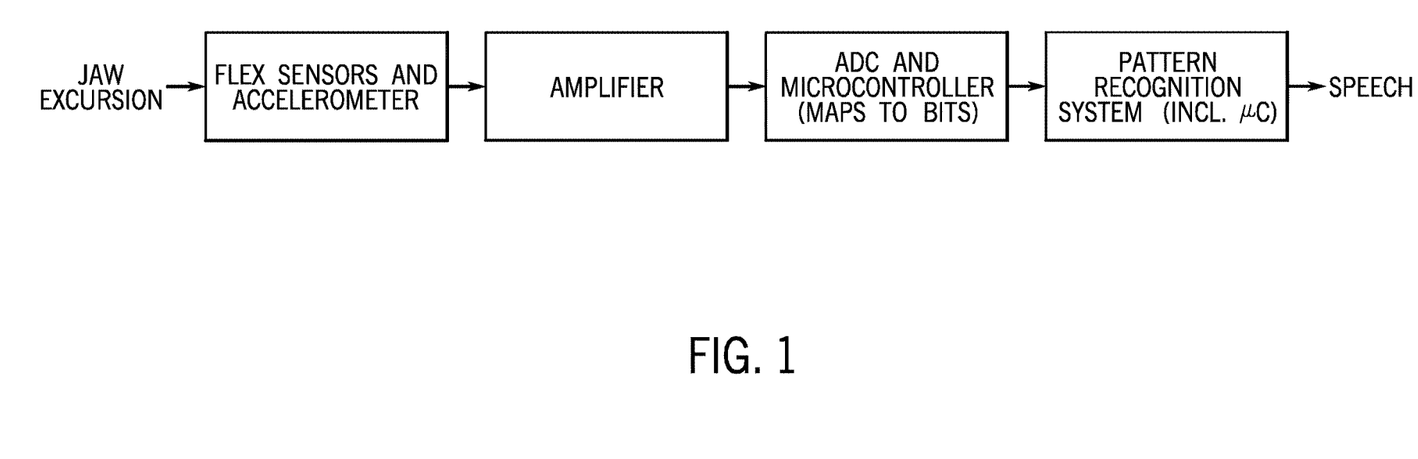
FIG. 1 shows a flow chart of components of an exemplary electrolarynx of embodiments of the present disclosure.
Figure 2:
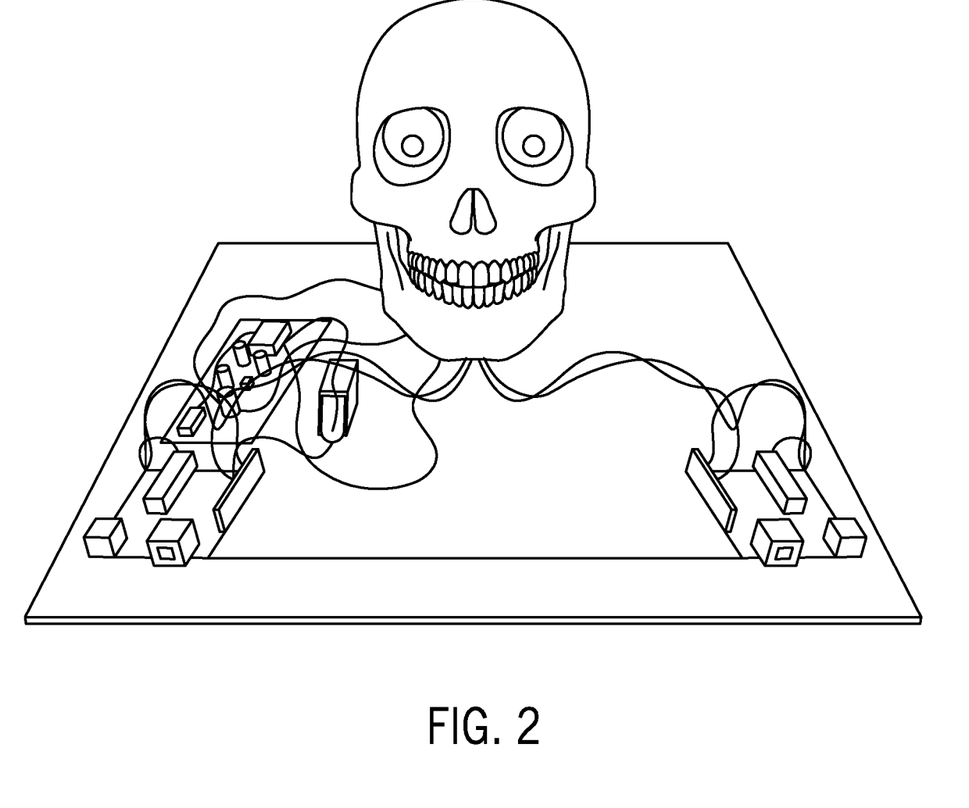
FIG. 2 shows a photograph of an exemplary device of embodiments of the present disclosure.
Figure 3:
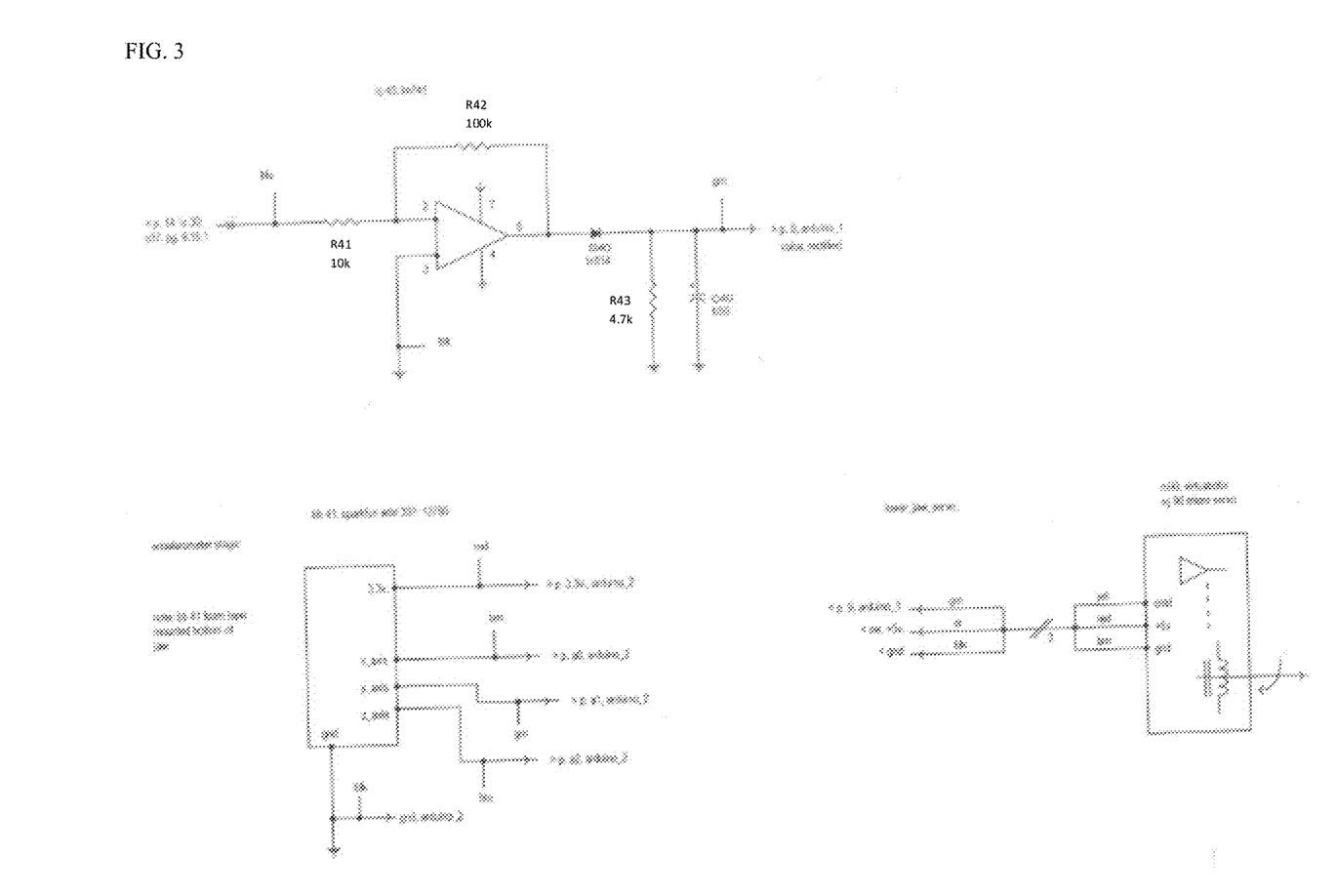
FIG. 3 shows electrical circuits of a servo control and accelerator monitoring element of exemplary devices of embodiments of the present disclosure.
Figure 4:
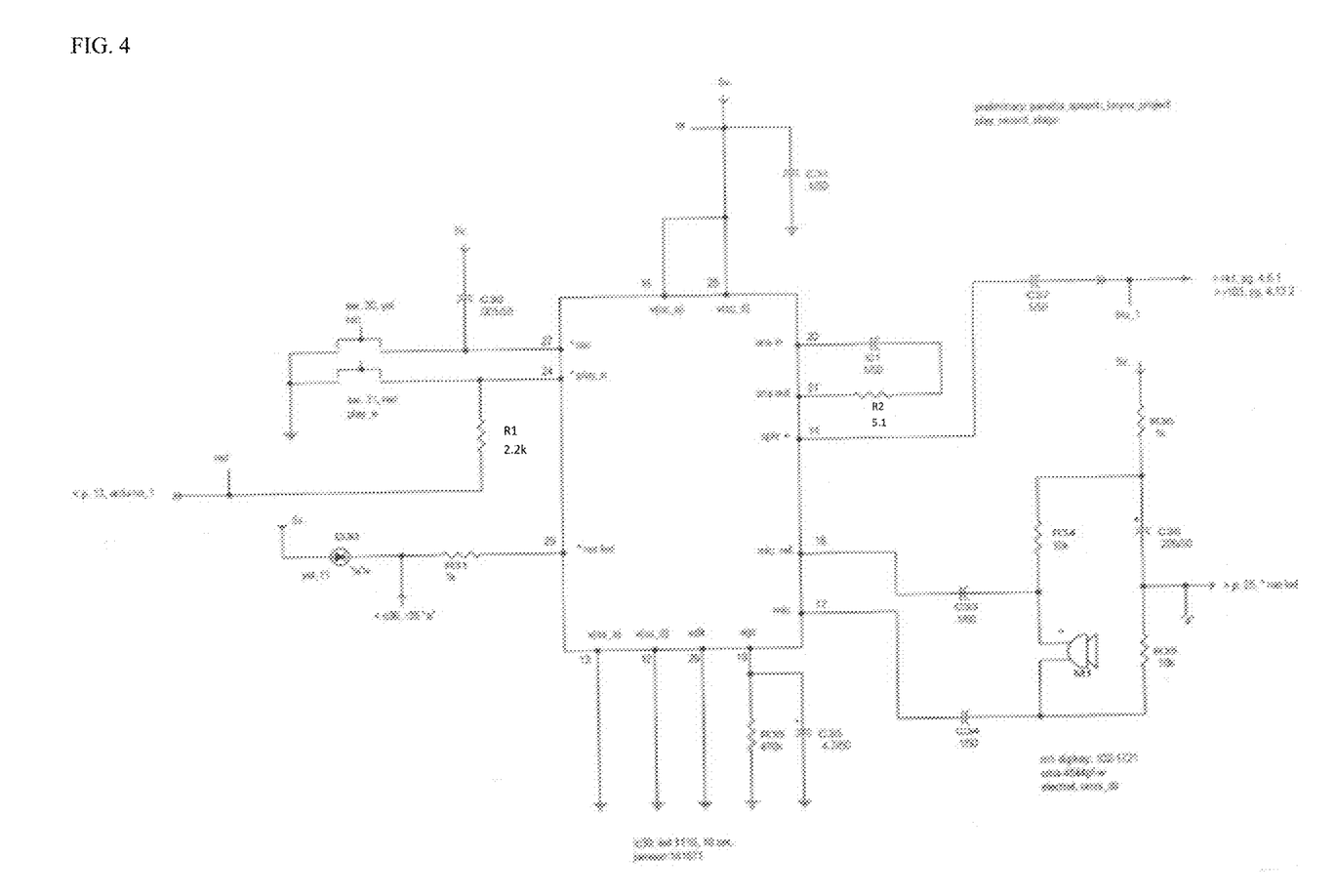
FIG. 4 shows electrical circuits of a playback stage for recording simulating speech of exemplary devices of embodiments of the present disclosure.
Figure 5:
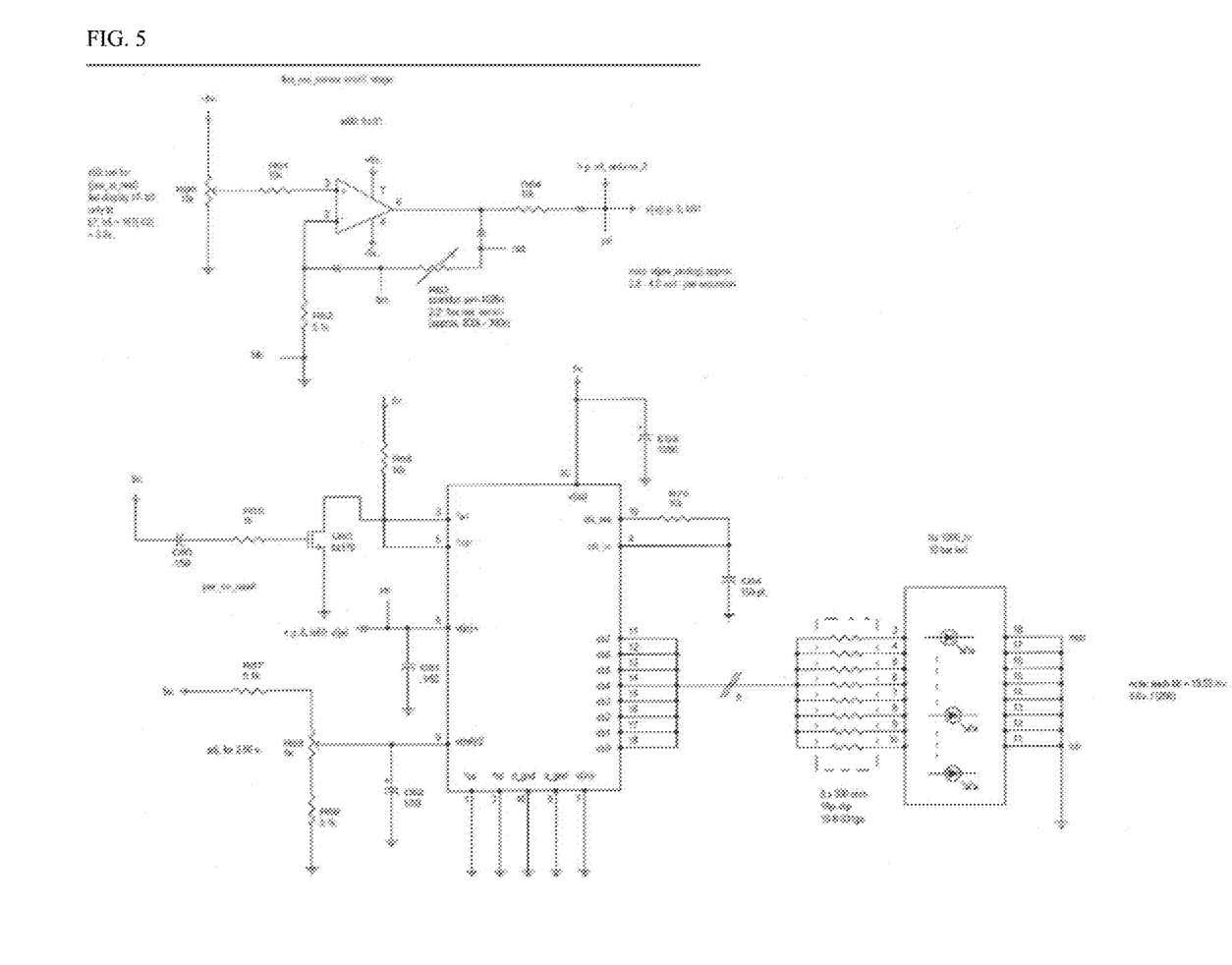
FIG. 5 shows electrical circuits of a flex-sensor amplifier and A/D stage of exemplary devices of embodiments of the present disclosure.
Figure 6:
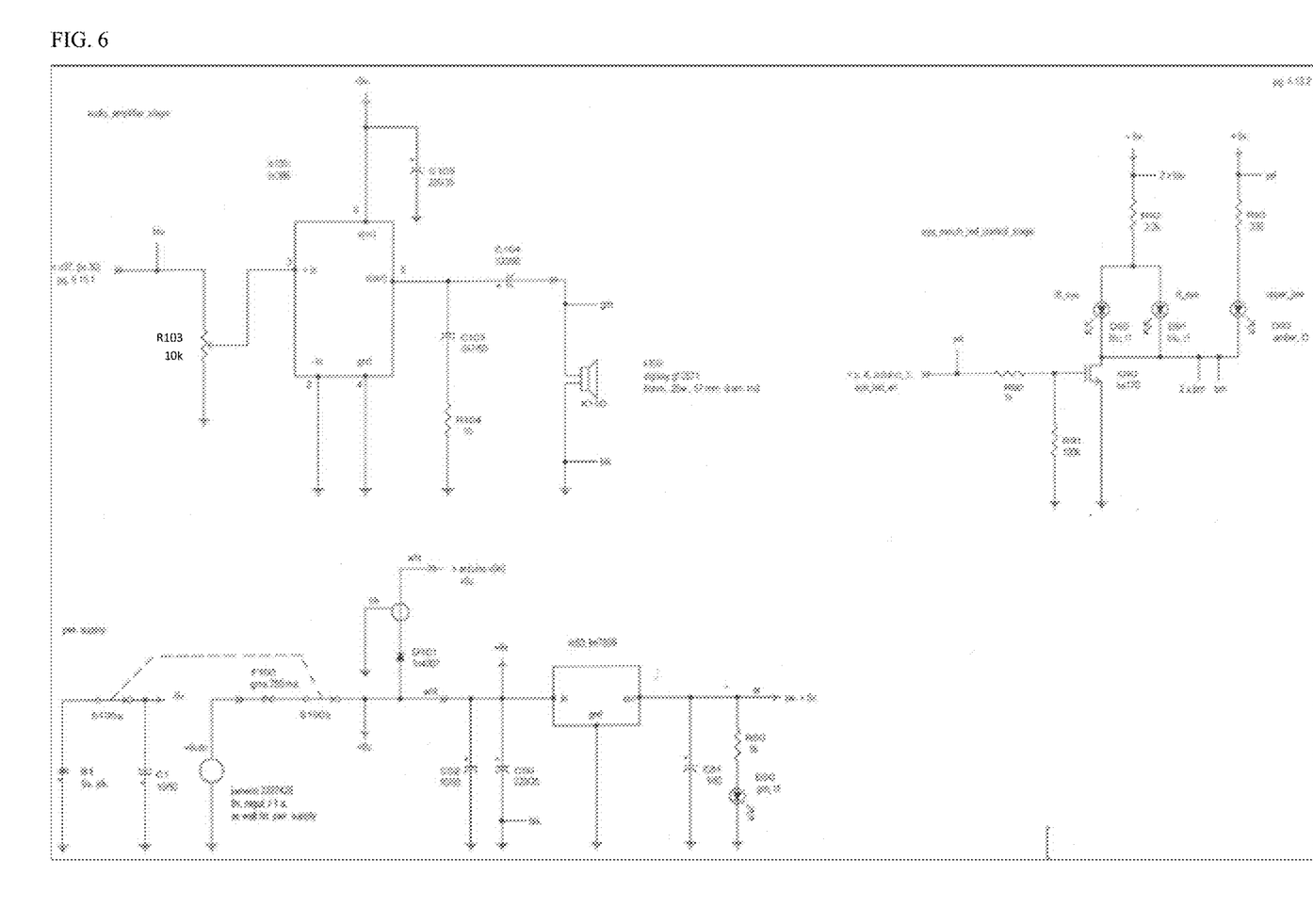
FIG. 6 shows electrical circuits of a power supply and audio amplifier element of exemplary devices of embodiments of the present disclosure.

A flow chart of an exemplary process for using the devices described herein is shown in FIG. 1. In use, a user speaks. The stoma sensor 1 transmits signal to control element 5, which senses that the speaker is talking and thus activates speaker 6. The control element 5 utilizes circuits and computer processor to translate stoma sensor into speech, which is transmitted through speaker 6. When the user is silent, the control center senses lack of speech from the stoma sensor 1 and turns off speaker 6.

All publications, patents, patent applications and accession numbers mentioned in the above specification are herein incorporated by reference in their entirety. Although the disclosure has been described in connection with specific embodiments, it should be understood that the disclosure as claimed should not be unduly limited to such specific embodiments. Indeed, various modifications and variations of the described compositions and methods of the disclosure will be apparent to those of ordinary skill in the art and are intended to be within the scope of the following claims.

We claim:

1. An electrolarynx system, comprising;
   a) a sensor configured to be placed in the stoma of a human subject;
   b) a control element controlled by said subject's breath or movement of said subject's jaw configured to obtain signal from said sensor and translate said signal into speech, wherein said control element is configured to turn said speaker on when said subject is talking and turn said speaker off when said subject is silent; and
   c) a speaker configured to amplify said speech.

2. The system of claim 1, wherein said control element comprises one or more of an electrical circuit, a computer processor, and computer memory.

3. The system of claim 1, wherein said control element is further configured to perform articulatory pattern recognition of said subject's speech.

4. The system of claim 1, wherein said signal is transmitted from said sensor to said control element via an electrical cable.

5. A method of generating artificial speech, comprising:
   contacting the system of claim 1 with a subject's stoma under conditions such that said device generates speech and transmit said speech through the speaker of said device.

6. The method of claim 5, wherein said subject lacks a larynx.

7. The method of claim 6, wherein said subject has previously been diagnosed with oral cancer.

8. The method of claim 6, wherein method is performed hands free.

\* \* \* \* \*